(12) United States Patent
Fegert et al.

(10) Patent No.: US 7,668,583 B2
(45) Date of Patent: Feb. 23, 2010

(54) METHOD AND APPARATUS FOR CONTROL AND LOCATION OF AN INSTRUMENT OR APPLIANCE

(75) Inventors: Stephan Fegert, Netphen (DE); Eckhardt Hoenig, Jena (DE); Wilfried Andrä, Jena (DE); Volkmar Schultze, Rutha (DE)

(73) Assignee: Rayonex Schwingungstechnik GmbH, Lennestadt (DE)

( * ) Notice: Subject to any disclaimer, the term of this patent is extended or adjusted under 35 U.S.C. 154(b) by 237 days.

(21) Appl. No.: 10/517,640

(22) PCT Filed: Jun. 10, 2003

(86) PCT No.: PCT/EP03/06048
§ 371 (c)(1),
(2), (4) Date: Jan. 4, 2005

(87) PCT Pub. No.: WO03/103492
PCT Pub. Date: Dec. 18, 2003

(65) Prior Publication Data
US 2005/0288576 A1    Dec. 29, 2005

(30) Foreign Application Priority Data
Jun. 10, 2002    (DE) ................. 102 25 518

(51) Int. Cl.
| A61B 5/05 | (2006.01) |
| E21B 25/16 | (2006.01) |
| A61B 19/00 | (2006.01) |
| A61B 1/00 | (2006.01) |

(52) U.S. Cl. ............... 600/424; 175/45; 128/899; 600/117

(58) Field of Classification Search .......... 600/409, 600/424, 117; 324/244; 128/899
See application file for complete search history.

(56) References Cited

U.S. PATENT DOCUMENTS

| 3,724,589 A |   | 4/1973 | Chapman, III |
| 4,791,373 A | * | 12/1988 | Kuckes ................. 324/346 |
| 5,002,137 A | * | 3/1991 | Dickinson et al. ......... 175/19 |
| 5,258,755 A | * | 11/1993 | Kuckes ................ 340/853.5 |

(Continued)

FOREIGN PATENT DOCUMENTS

DE    196 32 273 A1    2/1998

(Continued)

OTHER PUBLICATIONS

Sugita, Kei et al. "Study of Time Dependent Magnetic Field Variation Due to Current Redistribution in Rutherford Cable." IEEE Transactions on Applied Superconductivity, vol. 14, No. 2. (Jun. 2004): 255-258.*

Primary Examiner—Eric F Winakur
Assistant Examiner—Helene Bor
(74) Attorney, Agent, or Firm—Henry M. Feiereisen; Ursula B. Day

(57) ABSTRACT

The invention relates to an apparatus for location of an instrument or appliance having at least one magnet which produces a magnetic moment at right angles to the appliance shaft and can be rotated independently of the instrument or appliance. This results in a location system which allows precise location at an accurate time, determination of the axis direction and control of an appliance which is being operated in a channel or medium.

19 Claims, 16 Drawing Sheets

U.S. PATENT DOCUMENTS

| | | | |
|---|---|---|---|
| 5,265,682 A * | 11/1993 | Russell et al. | 175/45 |
| 5,353,798 A | 10/1994 | Sieben | |
| 5,589,775 A | 12/1996 | Kuckes | |
| 5,836,869 A | 11/1998 | Kudo et al. | |
| 5,882,304 A * | 3/1999 | Ehnholm et al. | 600/411 |
| 5,913,820 A * | 6/1999 | Bladen et al. | 600/407 |
| 5,961,465 A * | 10/1999 | Kelly et al. | 600/459 |
| 6,052,610 A * | 4/2000 | Koch | 600/424 |
| 6,102,137 A * | 8/2000 | Ward et al. | 175/45 |
| 6,248,074 B1 | 6/2001 | Ohno et al. | |
| 6,263,230 B1 * | 7/2001 | Haynor et al. | 600/424 |
| 6,381,485 B1 * | 4/2002 | Hunter et al. | 600/407 |
| 6,445,187 B1 * | 9/2002 | Montgomery et al. | 324/346 |
| 6,537,196 B1 * | 3/2003 | Creighton et al. | 600/12 |
| 6,755,791 B2 * | 6/2004 | Kawashima | 600/467 |
| 2004/0106863 A1 * | 6/2004 | Seki et al. | 600/409 |

FOREIGN PATENT DOCUMENTS

| | | |
|---|---|---|
| EP | 0 581 434 B1 | 8/1998 |
| EP | 1 181 891 A2 | 2/2002 |

\* cited by examiner

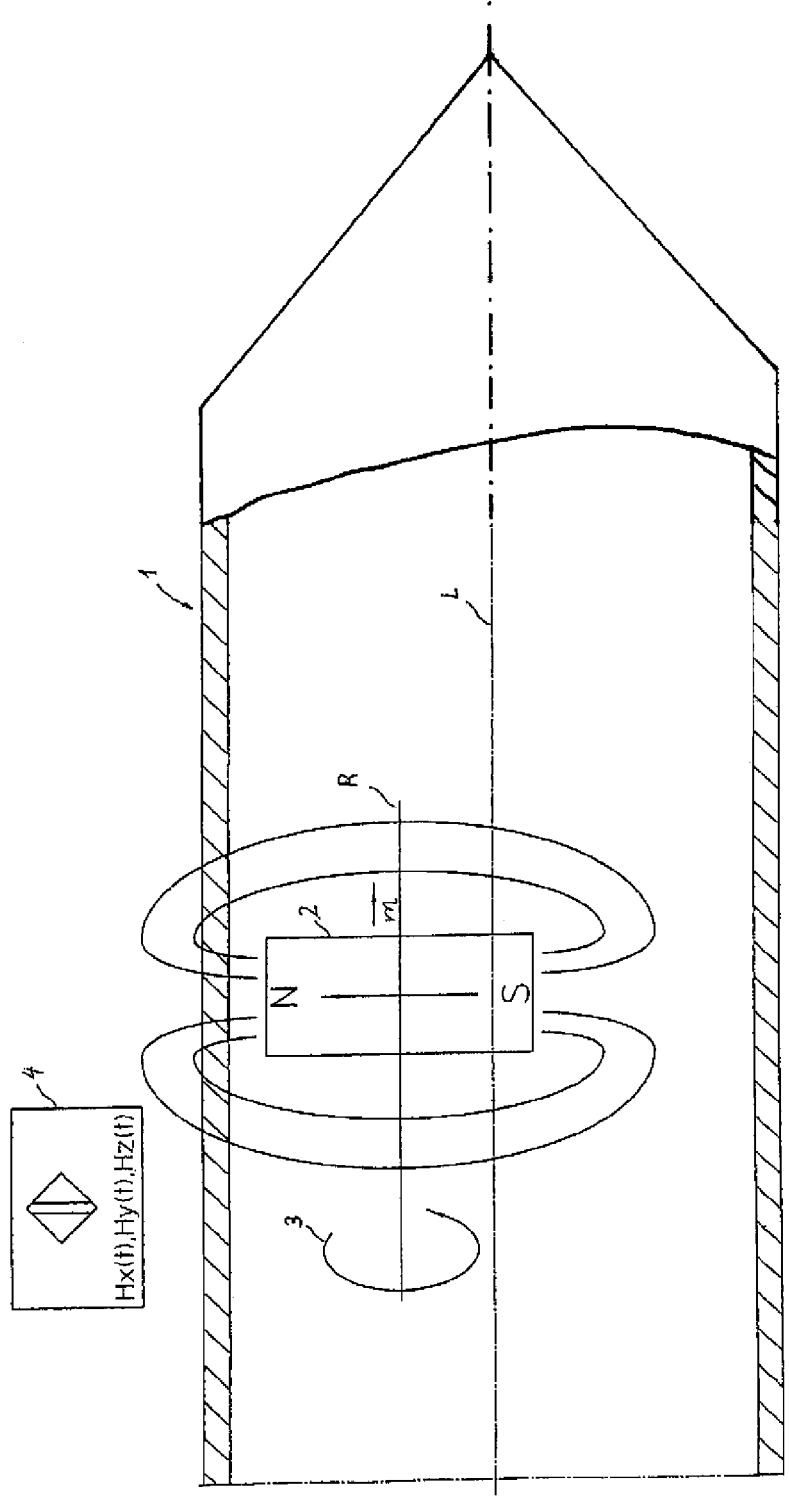

METHOD AND APPARATUS FOR CONTROL AND LOCATION OF AN INSTRUMENT OR APPLIANCE

BACKGROUND OF THE INVENTION

The invention relates to an apparatus for location and control of an appliance, as is preferably used for endoscopy or microsurgery.

Microsurgical and endoscopic instruments which are used in medicine are used in particular for diagnosis and during operations on sensitive tissues and organs to which access is difficult. These actions are generally computer-controlled and/or camera-controlled and normally require a very high degree of precise location, positioning and movement of the instruments. Probe systems such as magnetic or electromagnetic probes are used for this purpose. By way of example, U.S. Pat. Nos. 5,836,869 and 6,248,074 disclose fixed magnetic field sources and magnetic field sensors, respectively, which measure the three spatial coordinates of a moving magnetic field by means of a three-axis configuration of the magnet or, respectively, of the sensor. However, this does not allow spatially exact location of the endoscopic appliance at an accurate time. This is explained by the fact that the determination of the magnetic field co-ordinates as described in U.S. Pat. No. 5,836,869 necessitates the measurement of three different magnetic fields for a three-axis magnet which, in order to avoid superimposition, must be measured successively at different times, by the individual axes producing electromagnetic signals at different times. The measurement is in this case carried out outside the patient and also requires a conversion operation in order to make it possible to estimate the position of the endoscope in the body.

U.S. Pat. No. 6,248,074 discloses a magnetic field source being mounted outside the patient; the location process is in this case carried out by determination of the relative position of the detector with respect to the external magnetic field by means of a magnetic field sensor which is fitted to the distal end of the endoscope. In this case as well, only a relatively inaccurate measurement is possible, since the endoscope and sensor are moved with respect to the fixed magnetic field, so that there is no exact relationship between the fixed magnetic field co-ordinates and the variable spatial alignment of the sensor. Furthermore, there are additional impeding factors which adversely affect the accuracy, for example the problem of measuring regions at different distances from the body surface, or the adverse effect on measurement accuracy resulting from external magnetic fields. In contrast, probes which are introduced into the body interior are often very sensitive, but require complicated electrical cable systems or the continuous use and replacement of the batteries.

SUMMARY OF THE INVENTION

The invention is based on the object of providing a location system which allows precise location at an accurate time, determination of the axis direction and control of an appliance which is operated in a channel or medium.

The object is achieved by an apparatus and the method as claimed in the independent claims. Preferred embodiments are the subject matter of the dependent claims.

According to the invention, the location of the body, the direction of the body axis or feed axis and the roll angle of the body can be displayed via a connected evaluation unit, with the aid of the determined data.

For this purpose, the moving magnetic field is measured on three spatial axes. In this case, the data (amplitude, relative phase of the magnetic field components, axial field grading) of each spatial co-ordinate point in the magnetic field can be determined exactly. A three-axis magnetometer, such as a flux gate sensor, which is suitable for three-dimensional measurement may be used for this purpose.

A permanent magnet, for example a permanent magnet in the form of a rod, or alternatively an electromagnet is preferably used as the magnet.

The apparatus is preferably used for location, determination of the axis direction and control of a medical, microsurgical or endoscopic appliance.

In one preferred embodiment, the body, the appliance or the instrument is driven by rotation or carries out rotational movements during the process; in this case, the magnet may be firmly connected to the appliance shaft, and may rotate with it. This has the advantage that the roll angle of the appliance can always be determined exactly, since the position of the magnet is always related to the appliance shaft in a defined manner.

In one alternative embodiment, the magnet is driven by a separate drive independently of the appliance shaft. This drive may be provided electrically, for example by a battery or by a controllable electric motor; alternatively, it can also be provided by means of a liquid flowing through the appliance, for example a cooling liquid, or a gas.

Driving the magnet independently of the appliance shaft makes it necessary to provide defined reference points in order to determine the roll angle. For this purpose, the roll angle may be measured by means of a further variable component of the magnetic field, which is dependent on the roll angle of the appliance.

This further variable component of the magnetic field may, for example, be produced by reproducible deflection of the magnet from its rotation axis, temporary interruption of the rotation by means of a coupling, or provision of a magnet composed of two or more elements, whose elements which move with respect to one another reproducible shift by a driver at a specific roll angle. A further option is to vary the amplitude of the magnetic field by means of shielding which is dependent on the roll angle.

In one preferred embodiment, the appliance or the appliance tip is provided with at least one drill, a cutting or impact apparatus, a needle, a canular or a set of forceps.

This is particularly advantageous for carrying out operations, such as actions on the brain, heart or intestinal tract, for the implantation of organ, tissue or vessel spare parts, catheters, probes and pacemakers, or for the removal or destruction of inflamed or malign tissues, bone and cartilage tissue or for the treatment of kidney stones etc. If the magnet is also moved with the rotation of the appliance, it is also possible to measure the rotation rate or a change in the rotation rate.

Alternatively, the appliance or the appliance tip may be provided with one or more openings for emission of a liquid. This is particularly advantageous in order to release therapeutic substances, such as cytostatica for tumor therapy, in liquid or dissolved form, as accurately as possible. If the magnet is driven by the liquid flow, it is also possible to measure the flow rate and emission rate of the solution.

In one further preferred embodiment, the appliance or the appliance tip contains an apparatus for production or emission of light beams, laser beams, radioactive beams, sound waves or ultrasound waves.

In one particularly preferred embodiment, the appliance or appliance tip contains an apparatus for recording optical images or ultrasound images. This is particularly advantageous for diagnosis in body cavities, the digestive tract and in vessels.

Alternatively, apparatuses may also be included for the emission or recording of electrical pulses and data.

Beams and acoustic waves may be produced not only for diagnostic purposes, such as tissue irradiation or the destruction of stones, but also for diagnostic purposes for the production of images or for the examination of organs, body cavities or blood vessels.

Apparatuses for the recording of images or electrical data are in turn used for known diagnostic purposes, while electrical signals are primarily emitted for therapeutic purposes, for example during specific pain therapy.

The described apparatuses and applications can also be used not only for the determination of the accurate position, alignment and rotation of the appliance but also for determination of the distance and direction of at least two measurement points or measurement areas with respect to one another. In this case, the relative position of the magnetic sensor (first measurement point) is determined with respect to the detector (second measurement point).

In this case, the detector may be positioned in a fixed or moving form outside or inside the body. In one preferred embodiment, the detector is connected to apparatuses for controlling the appliance and/or to apparatuses which are connected to the appliance.

One particular advantage is the capability to measure the position and movement of the appliance exactly and at an accurate time, that is to say in "real time". The use of two or more transmitters and/or receivers also makes it possible to record complex signals, which can indicate the position of different appliance points.

Furthermore, an electrically driven magnet can be used, with communication or control signals being produced between the magnetic transmitter and the detector by interrupting the electrical magnetic drive on a specific clock cycle (yes/no states).

A further advantageous embodiment is based on the capability to vary the frequency or amplitude of the magnetic field. In this case, the amplitude may be modulated in order to produce frequency-selective amplification, to minimize the influence of disturbing external magnetic fields or, when two or more magnetic probes are used, to distinguish between them.

However, the invention is not restricted to use in the medical field; the apparatuses and methods according to the invention can equally also be used in other scientific or technical areas in which it is necessary to precisely locate and control instruments or appliances.

According to the invention, the arrangements and methods in the independent claims are used to determine the position of a drilling head, the rotation axis of a drilling rod or the feed direction of a drilling tool, as well as the roll angle of a drilling appliance or drilling head, with the position, axis and roll angle of the magnet being used as actual measurement variables, while, in the case of known methods, it is possible to determine only the position and the roll angle, but not the feed direction (U.S. Pat. No. 5,589,775).

The relevant drilling appliances are preferably controllable drilling systems, underground rockets, hammer drilling appliances or bursting and widening apparatuses.

In this case, the magnet may be firmly connected to the linkage, thus assuming a permanently defined roll angle with respect to the linkage, or maybe caused to rotate by means of a separate drive in the transmitter housing of the drill. In addition, when a magnet is firmly connected to the linkage, the magnet may be rotated independently of the other appliance parts, provided that these appliance parts can move with respect to the linkage. In order to relate the roll angle of the magnet and of the drilling head to one another in a defined manner, a further variable component of the magnetic field can be measured, which is dependent on the roll angle of the drilling head or linkage.

For this purpose, the magnet can be stopped in a precisely defined relative position with respect to the drilling head after the separate drive has been switched off, by means of a suitable apparatus. At this moment, the magnet is once again firmly connected to the linkage, and the roll can then be measured, set or varied by rotation by means of the linkage.

Alternatively, the magnet may be tilted from its rotation axis one or more times during rotation. A cam which is connected to the transmitter housing may be used for this purpose. This fixed connection of the stop to the transmitter housing means that the deflection is always in a defined position relative to the control surface of the drilling head.

In a further embodiment, the magnet is briefly stopped by a coupling, and is then driven again.

Alternatively, the magnet may comprise two or more magnet elements, which are rotated with respect to one another for a short time by means of a driver, thus varying the strength and alignment of the magnetic field.

A further option is to shield the magnetic field while passing through a specific angle range.

Details have already been described in the present invention description for other application fields; they can each be used for any desired application fields.

Various methods may be used to measure the magnetic field: the receiver may be moved relative to the transmitter as a standard walk-over receiver, and it may likewise be fixed to the drilling appliance or at any desired point for this purpose, with the position relative to the drilling appliance and drilling plan in each case being known. In order to determine, or to enlarge, the maximum range of a receiver, different positions may be measured; the receiver is then moved to the respective next position during the measurement.

Instead of measuring different points in sequence, two or more transmitters may be used, for example a transmitter on the drilling head and a transmitter on the drilling appliance. In this case, the receiver may be used as a walk-over receiver, in which case absolute measurement in a co-ordinate system formed by the transmitters is nevertheless possible by the measurement of two points.

In a further preferred embodiment, the receiver has a drilling plan program and a display apparatus. This allows remote control of the drilling process. In this case, the actual and nominal path may be displayed with or without being linked to the drilling appliance, which also allows the drilling process to be carried out automatically, in addition to by remote control.

Instead of arranging the rotating magnets in the area of the drilling head, a receiver, for example a three-axis magnetometer, may also be arranged in the area of the drilling head. This makes it possible to cause a magnet of any desired size and any desired strength to be rotated outside the drilling appliance. This embodiment is suitable, for example, for oil drilling systems, owing to its very long possible range. In this case, flux gate sensors may be used in the drilling head, instead of gyroscopic systems, which are sensitive to impacts.

It is particularly advantageous in this case for the receiver to be connected to the drilling appliance, and for it to be controlled by means of a drilling plan program, without the use of wires.

The capability to measure the azimuth even from long distance results in a further advantage of the invention. In the case of the known methods, it is generally necessary to determine the azimuth, that is to say the angle between the north direction and the direction with reference to the respective target points of the measurement, directly via the transmitter.

The invention also offers the capability to change the transmitted data as well, or to link the data to form complex signals and codes. Conventional methods such as frequency-selective amplification, frequency modulation, amplitude modulation or combinations of them may be used in this case. In the case of frequency modulation, the rotation speed is varied. In the case of amplitude modulation, shielding can be provided, and is used to attenuate the magnetic field. Simple signals such as yes/no states can be provided by switching on and off coded in a similar manner to Morse Code. In this case, the signals may be transmitted in analog or digital form. In the case of analog transmission, continuously varying values can also be transmitted by gradually inserting the magnet into a shield or by gradual variation of the power supply to an electromagnet, while, in contrast, a coded switching-off mechanism can transmit digital values. A system such as this makes it possible, for example, to transmit signals in analog or digital form to the Earth's surface for a tensile force measurement system that is moved underground. Bidirectional transmission is likewise possible by fitting a receiver to the drilling head as well.

In embodiments with two or more transmitters, these transmitters can be distinguished with the aid of the invention by setting different transmitter frequencies.

There are a wide range of possible technical applications for the system according to the invention. The majority of these are based or measurement of the distance, the position and orientation, the direction or rotation of two or more bodies relative to one another or to an absolute reference point, and/or on recording and/or controlling movements.

The following possible applications are mentioned by way of example:

The system according to the invention is particularly suitable for carrying out precision drilling operations ("wormhole drilling operations").

Furthermore, all types of lines, channels and cavities can be investigated or examined precisely and at an accurate times by means of this system. In this case, the magnet may be mounted on a flexible shaft, and may be moved forwards or rotated.

In the case of tunnel construction, icing holes may be introduced in order to prevent collapse or the ingress of water and mud in the case of strata which carry large amounts of water. In this case, the drilling operations must be carried out very accurately in order to achieve a closed ice layer.

A further preferred application option is the control of driverless transport systems. At least one stationary receiver may be positioned for this purpose, which analyses the coded transmitters (transmitters at different frequencies). A magnet which rotates to a greater extent can, alternatively and without coding, be positioned in space, and can supply data to two or more receivers. This method allows control through obstructions, and there is no need for induction loops.

The analysis of the movement of two bodies with respect to one another can be used for various further applications, for example for automatic separation control in road traffic or for separation control during the refueling of aircraft, in which case appropriate safety systems can be initiated by signal transmission.

Further possible applications include navigation systems for watercraft, automatic anchor monitoring for watercraft, and the provision of communication systems for submarines. The use of modulated magnetic transmitters also makes it possible to provide communication systems which are proof against monitoring.

Further technical fields of application include controlled or automatic coupling apparatuses for drilling platforms, transmitters for data transmission in mines, transmitters for locating those buried in mining accidents or in avalanches. In this case, portable mini-transmitters can be used for the last-mentioned application and, for example, could be worn in a similar way to a watch.

BRIEF DESCRIPTION OF THE DRAWINGS

The present invention will be more readily apparent upon reading the following description of embodiments of the invention with reference to the accompanying drawing, in which:

FIG. 16 is a sectional view of the apparatus of FIG. 1, illustrating an instrument provided with a needle.

DETAILED DESCRIPTION OF THE DRAWINGS

Figure 1:
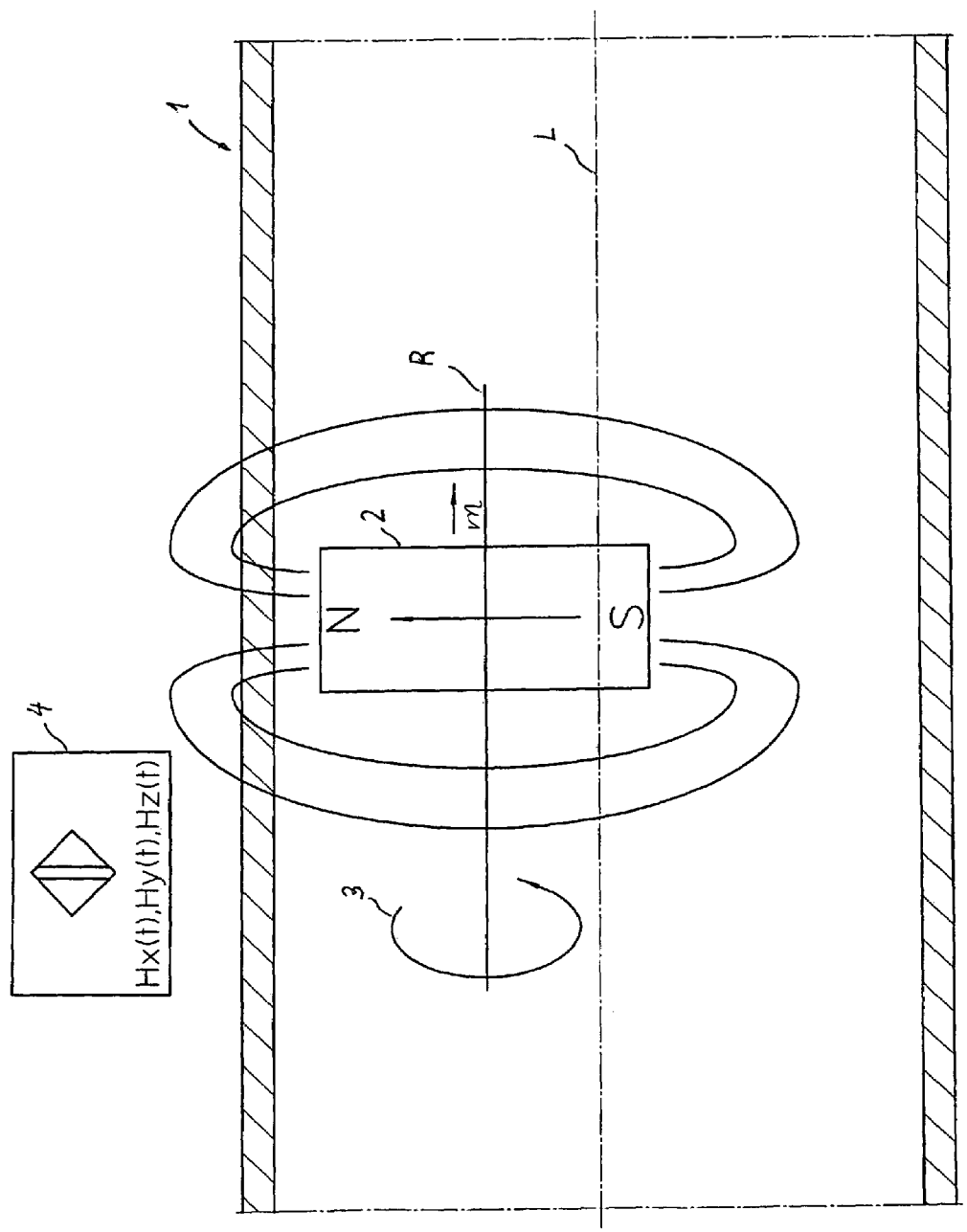
FIG. 1 is a sectional view of an apparatus embodying the subject matter of the present invention.

Turning now to the drawing and in particular to FIG. 1, there is shown a sectional view of an apparatus embodying the subject matter of the present invention for determining location and control of a body, an appliance or instrument, generally designated by reference numeral 1 and defining a longitudinal axis L. For sake of simplicity, the following description relates to instrument only. Disposed in the instrument 1 is a magnet 2 which is rotatable about a rotation axis R, as indicated by arrow 3, and whose moving magnetic field is measured on three spatial axes. The rotation axis R extends hereby in spaced-apart parallel relationship to the longitudinal axis L of the instrument 1. Thus, the magnet 2 produces a magnetic moment m which is perpendicular to the longitudinal axis L. Data (amplitude, relative phase of the magnetic field components, axial field grading) of each spatial co-ordinate point in the magnetic field can be determined exactly. A three-axis magnetometer, such as a flux gate sensor, which is suitable for three-dimensional measurement may be used for this purpose. The magnet 2 may also be implemented as permanent magnet, for example a permanent magnet in the form of a rod, or alternatively an electromagnet may be used as the magnet 2. The magnetic field is measured by a receiver 4, indicated schematically on top of FIG. 1, for detecting the three time-dependent magnetic field components Hx(t), Hy(t) and Hz(t).

Figure 2:
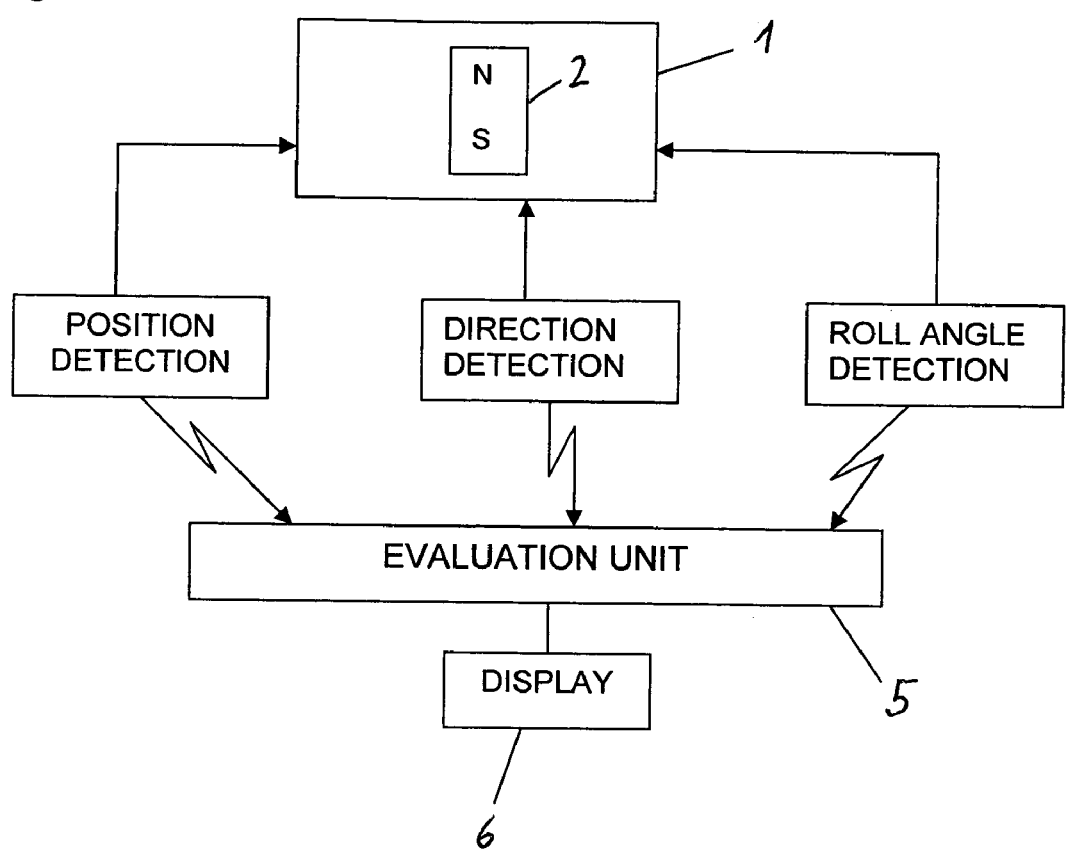
FIG. 2 is a schematic block diagram showing the relationship of components of the apparatus.

FIG. 2 is a schematic block diagram showing the relationship of components of the apparatus for determining the location of the instrument 1, the direction of the instrument axis or feed axis and the roll angle of the instrument 1 can be displayed via a connected evaluation unit 5 on a display 6, with the aid of the determined data.

Figure 3:
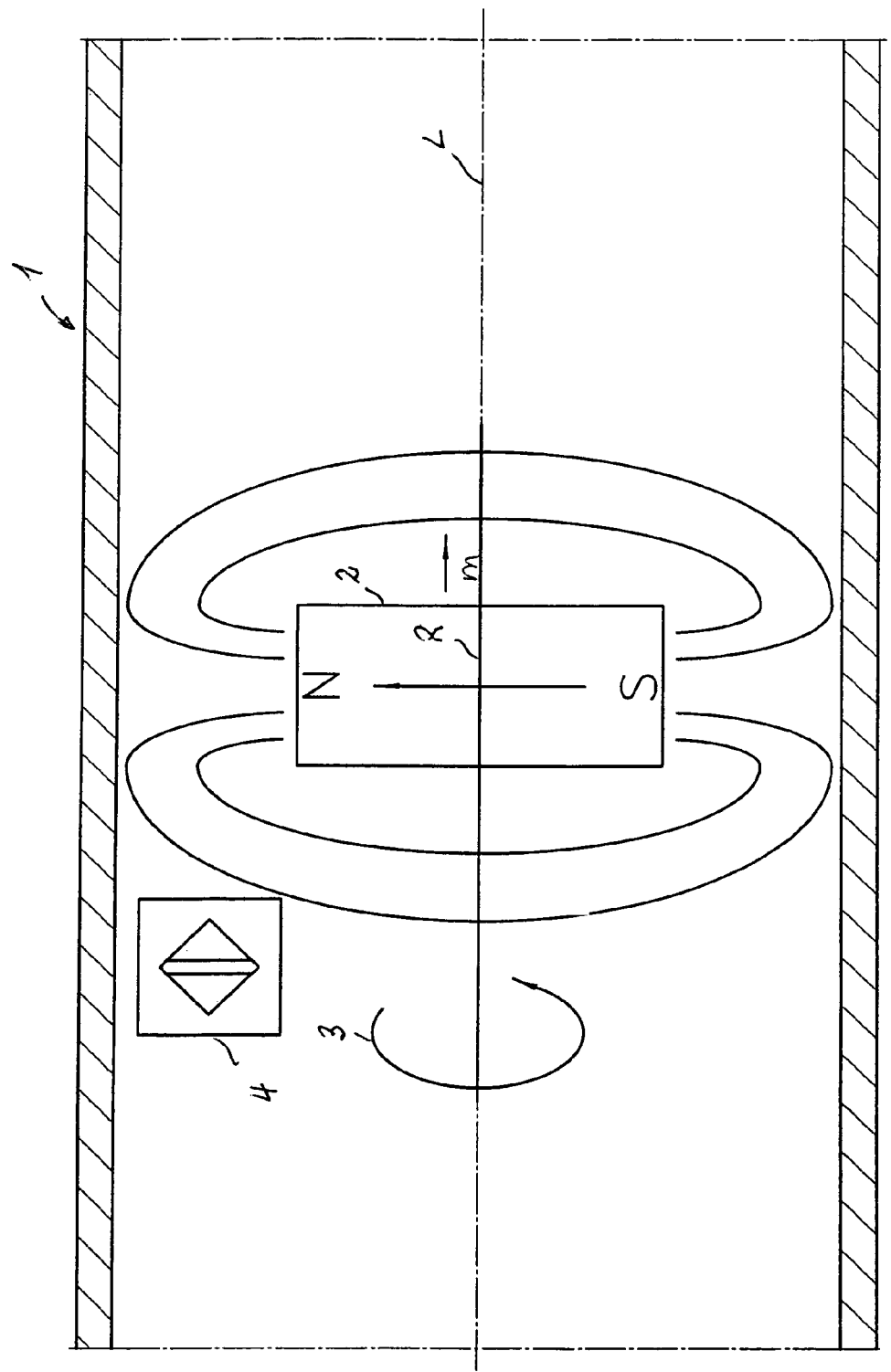
FIG. 3 is a sectional view of a variation of the apparatus according to the present invention.

FIG. 3 is a sectional view of a variation of the apparatus according to the present invention. Parts corresponding with those in FIG. 1 are denoted by identical reference numerals and not explained again. The description below will center on the differences between the embodiments. In this embodiment, the rotation axis R of the magnet 2 is in coincidence with the longitudinal axis L of the instrument 1.

Figure 4:
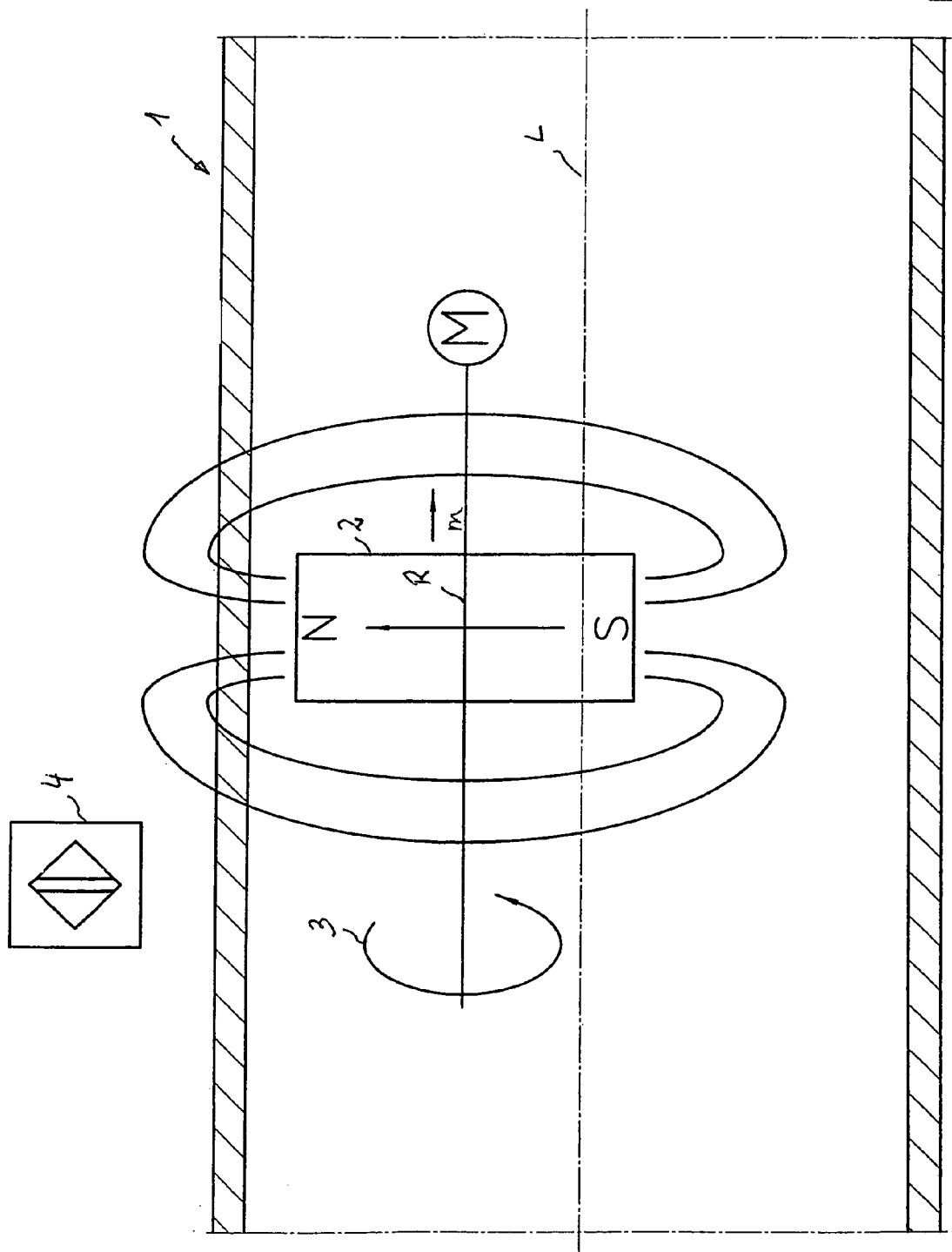
FIG. 4 is a sectional view of yet another variation of the apparatus according to the present invention.
Figure 5:
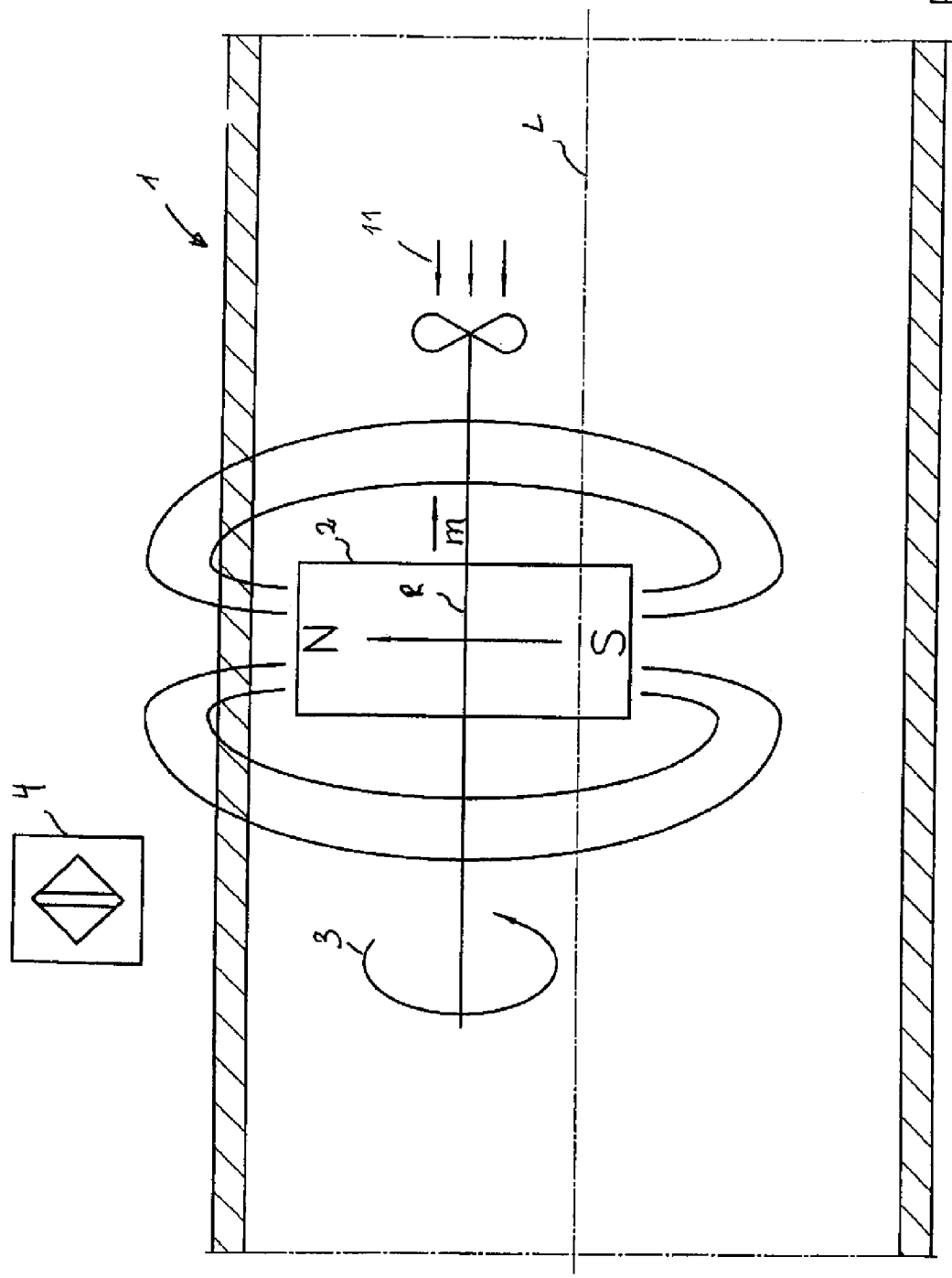
FIG. 5 is a sectional view of still another variation of the apparatus according to the present invention.

FIG. 4 is a sectional view of yet another variation of the apparatus according to the present invention in which the magnet 2 is driven by a separate drive M independently of the instrument axis L. This drive M may be provided electrically, for example by a battery or by a controllable electric motor; alternatively, it can also be provided by hydraulic means of a liquid flowing through the instrument 1, for example a cooling liquid, or a gas, as shown in FIG. 5 by way of arrows 11.

Figure 6:
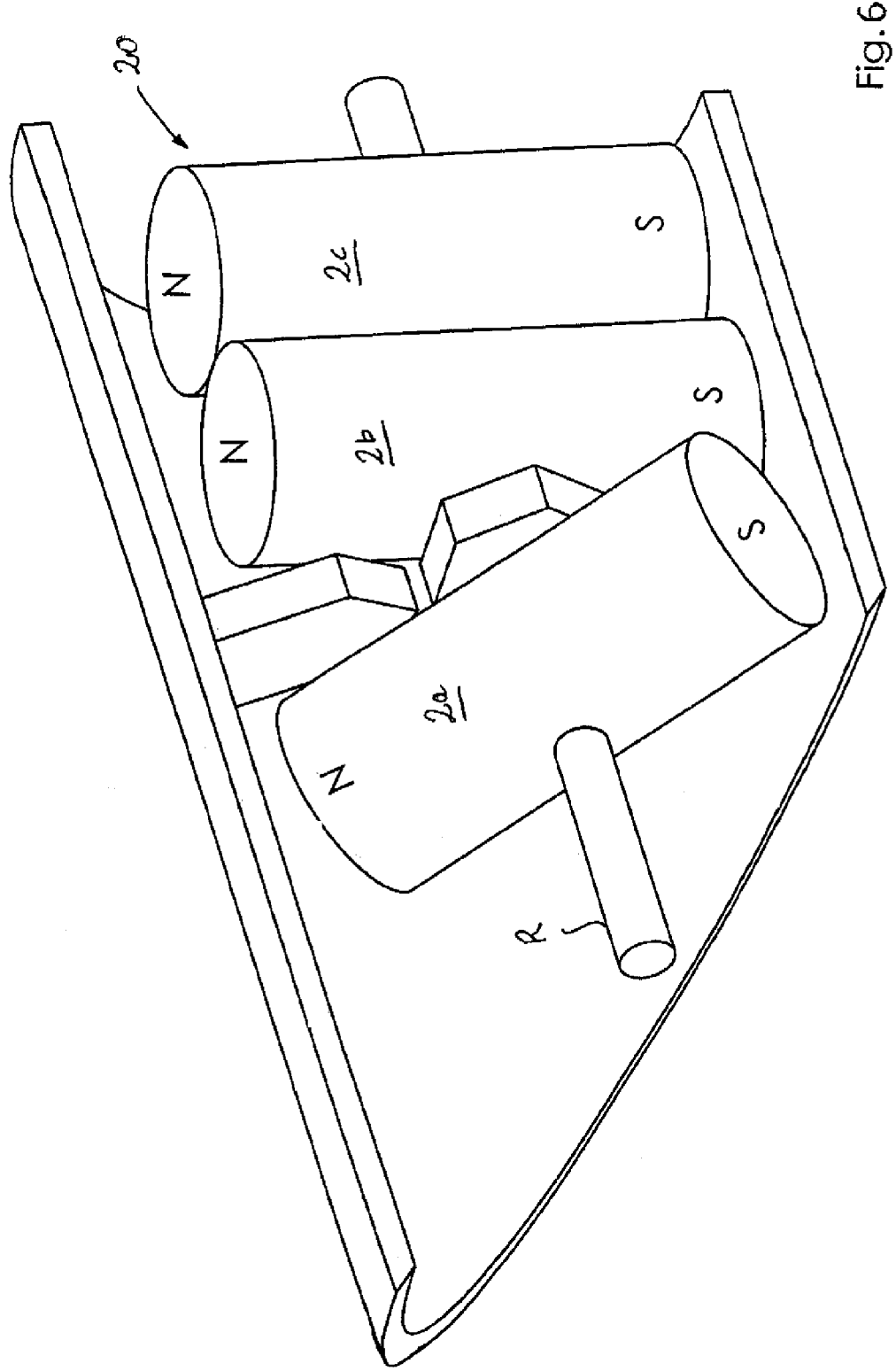
FIG. 6 is a perspective view of a magnet assembly for use in the apparatus according to the present invention.
Figure 7:
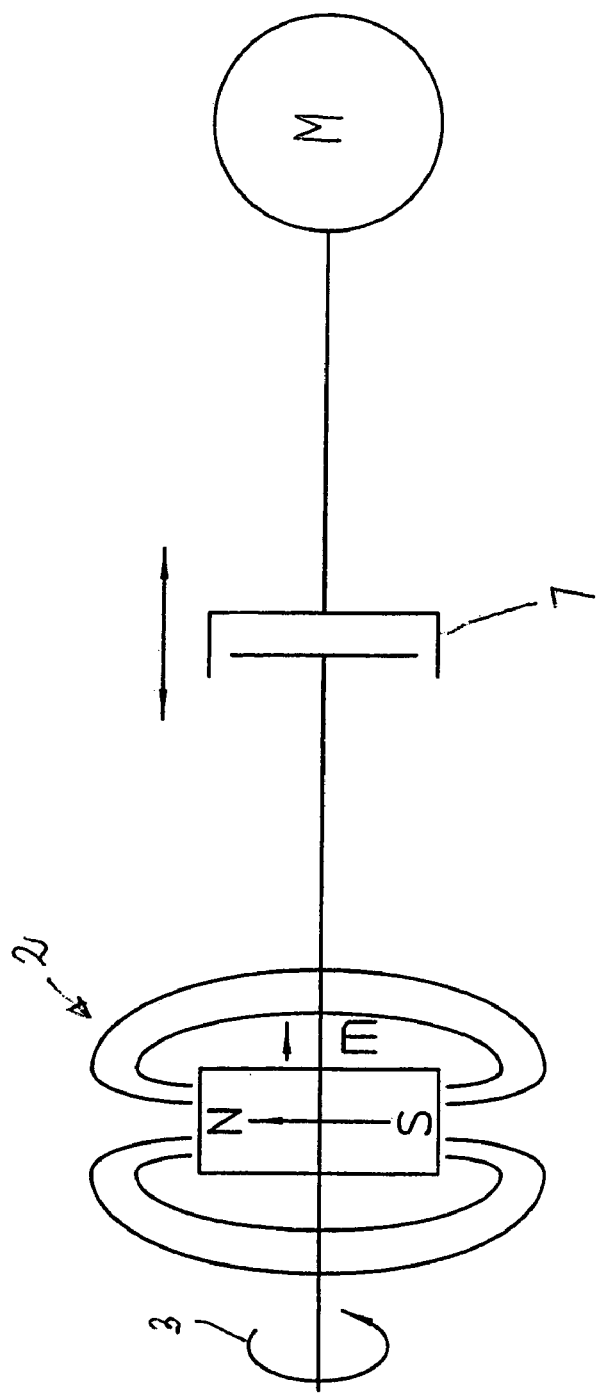
FIG. 7 is a schematic illustration of a variation of the apparatus of FIG. 4.

FIG. 6 is a perspective view of a magnet assembly 20 for use in the apparatus according to the present invention. The magnet assembly 2Q includes three magnets 2a, 2b, 2c, of which the magnet 2a is moveable in relation to the other magnets 2b, 2c by a driver at a specific roll angle. As a result of this reproducible deflection of the magnet 2a from its rotation axis R, it is possible to temporarily interrupt the rotation of magnet 2a by means of a coupling 7 disposed between the drive M and the magnet 2, as shown in FIG. 7. A further option is to vary the amplitude of the magnetic field by means of shielding which is dependent on the roll angle.

Figure 8:
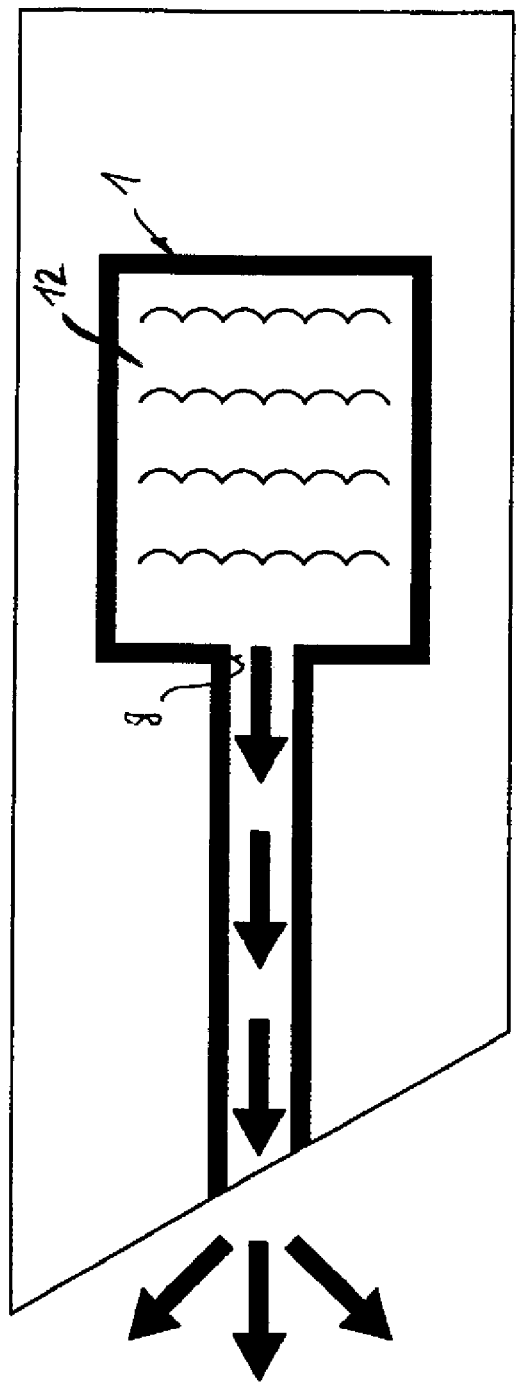
FIG. 8 is a schematic illustration of an instrument for use in the apparatus according to the invention.
Figure 9:
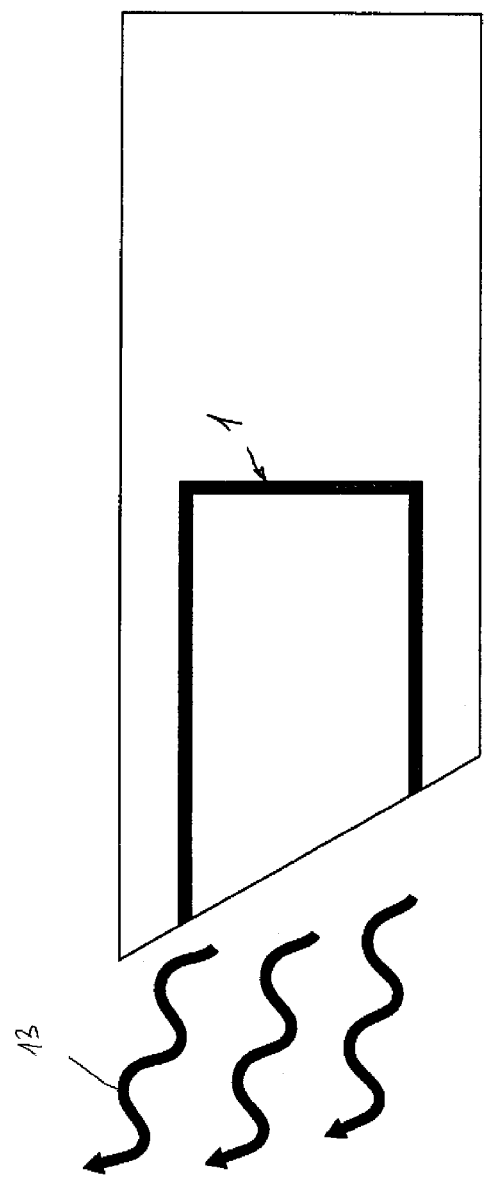
FIG. 9 is a schematic illustration of another instrument for use in the apparatus according to the invention.
Figure 10:
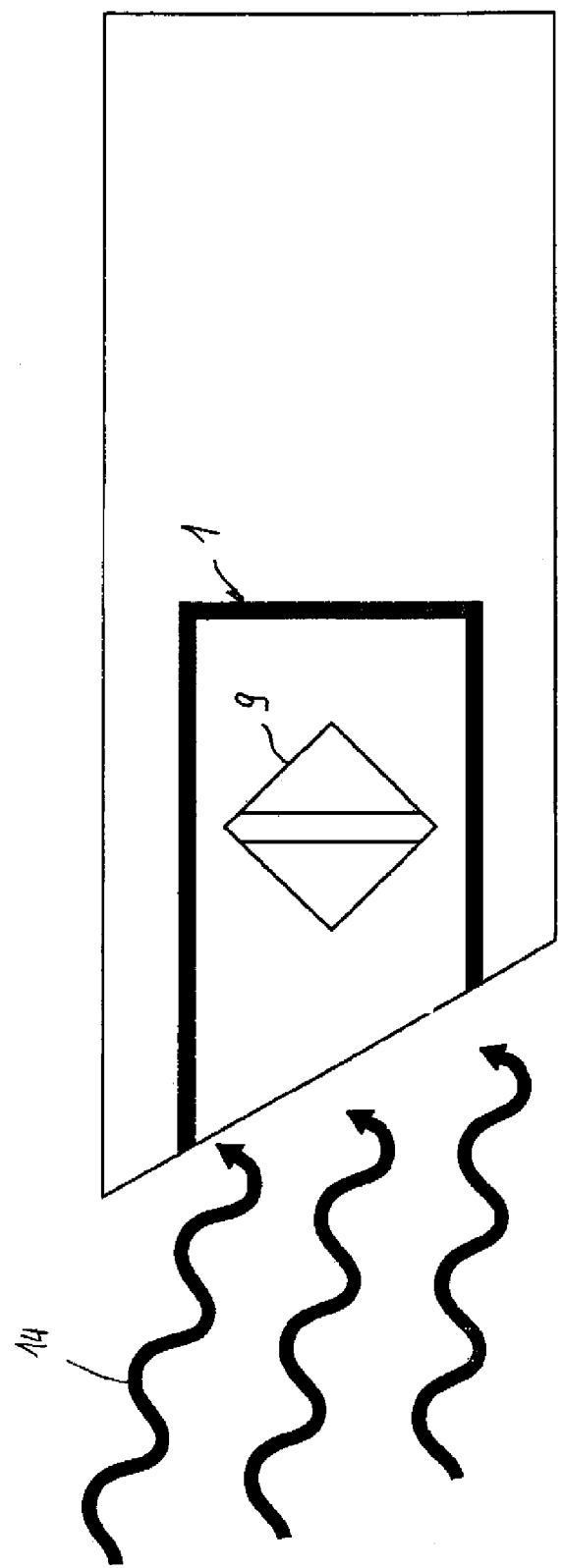
FIG. 10 is a schematic illustration of yet another instrument for use in the apparatus according to the invention.
Figure 11:
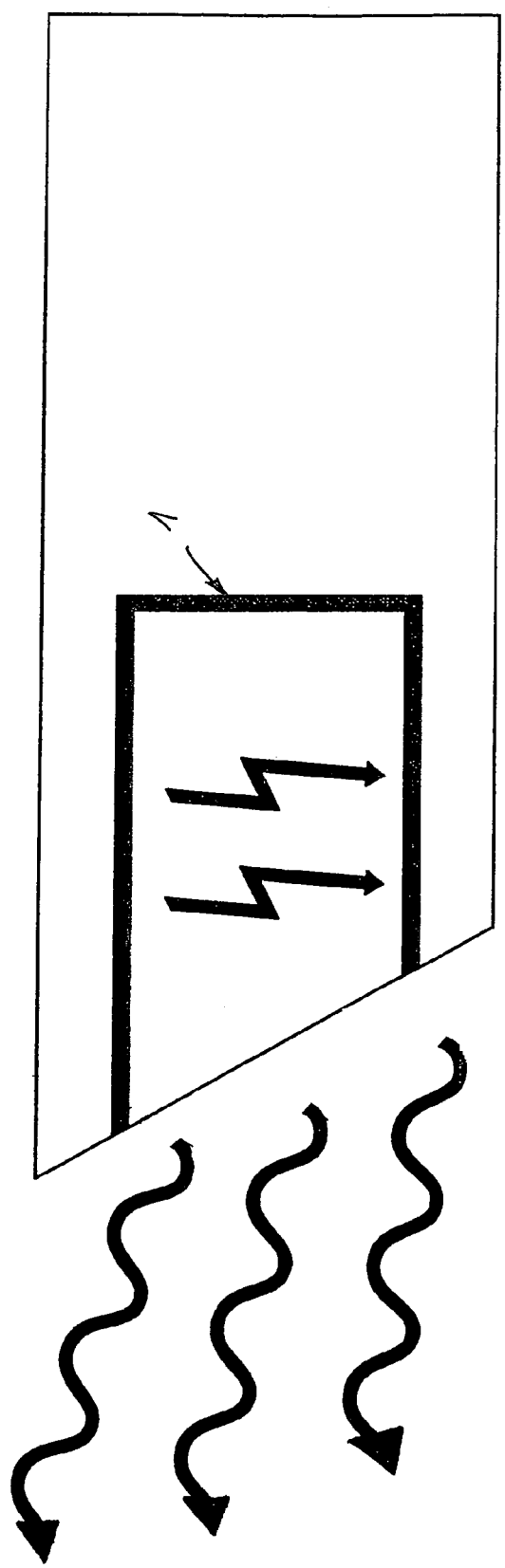
FIG. 11 is a schematic illustration of still another instrument for use in the apparatus according to the invention.

Referring now to FIG. 8, there is shown a schematic illustration of an instrument 1 which is provided with one or more openings 8 (only one opening 8 is shown here) for emission of a liquid 12. As a result, therapeutic substances, such as cytostatica for tumor therapy, in liquid or dissolved form, can be released as accurately as possible. If the magnet 2 is driven by the liquid flow, it is also possible to measure the flow rate and emission rate of the solution. As shown in FIG. 9, the instrument 1 contains a device for production or emission of light beams, laser beams, radioactive beams, sound waves or ultrasound waves, as indicated by reference numeral 13. In FIG. 10, the instrument 1 contains a device 9 for recording incident optical images or ultrasound images, as indicated by reference numeral 14. This allows diagnosis in body cavities, digestive tract and vessels. It is also possible to provide the instrument 1 with a device for emitting or recording of electrical pulses and data, as shown in FIG. 11, and indicated by reference numeral 15.

Figure 12:
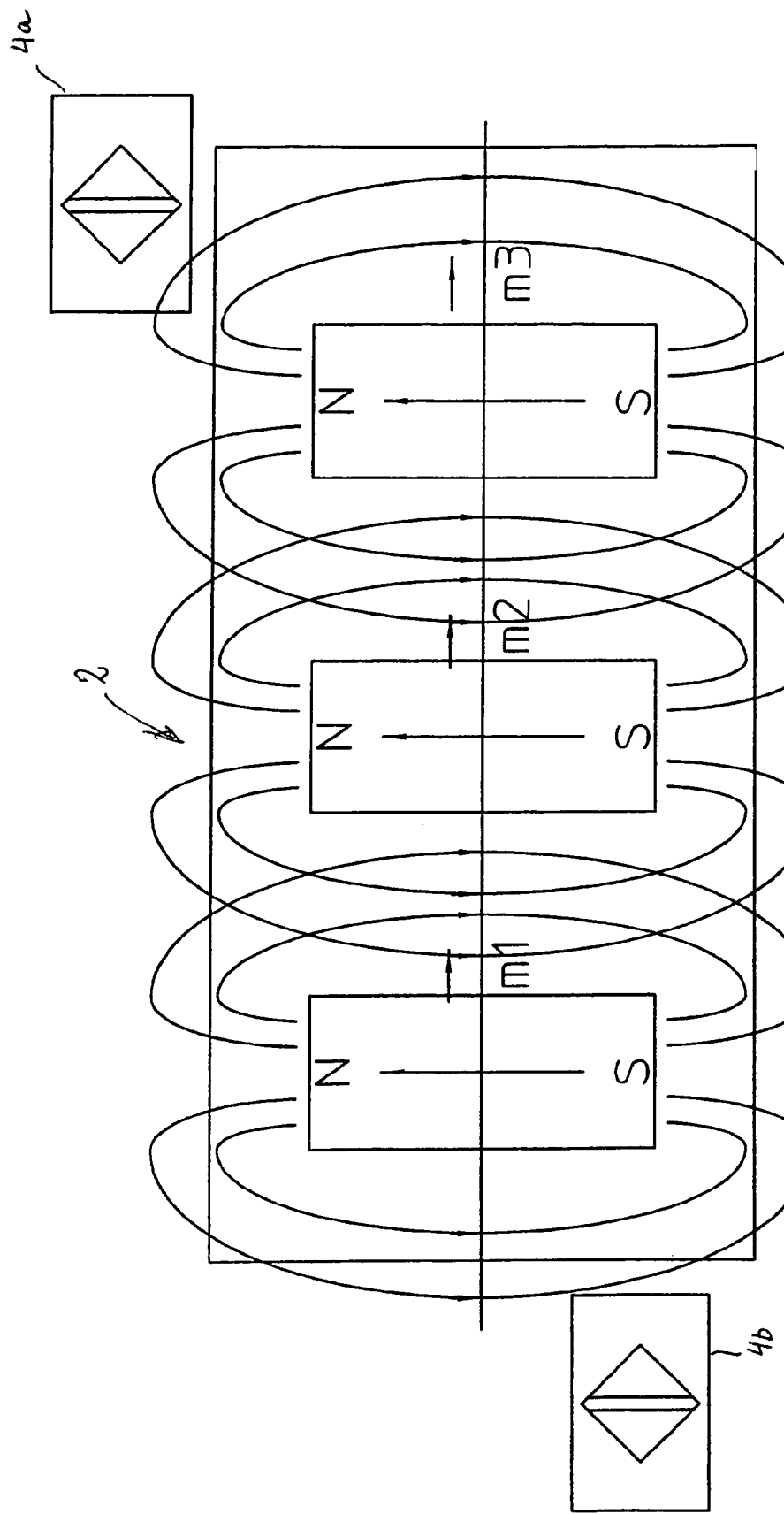
FIG. 12 is a schematic illustration of another magnet assembly for use in the apparatus according to the present invention.

FIG. 12 is a schematic illustration of another magnet assembly, generally designated by reference numeral 20 and including three magnets producing magnetic moment m1, m2, in m3, respectively. The magnet assembly 20 is provided to measure the position and movement of the instrument 1 (not shown here) exactly and at an accurate time, i.e. in "real time". The use of two or more transmitters and/or receivers 4a, 4b also makes it possible to record complex signals, which can indicate the position of different instrument points.

Figure 13:
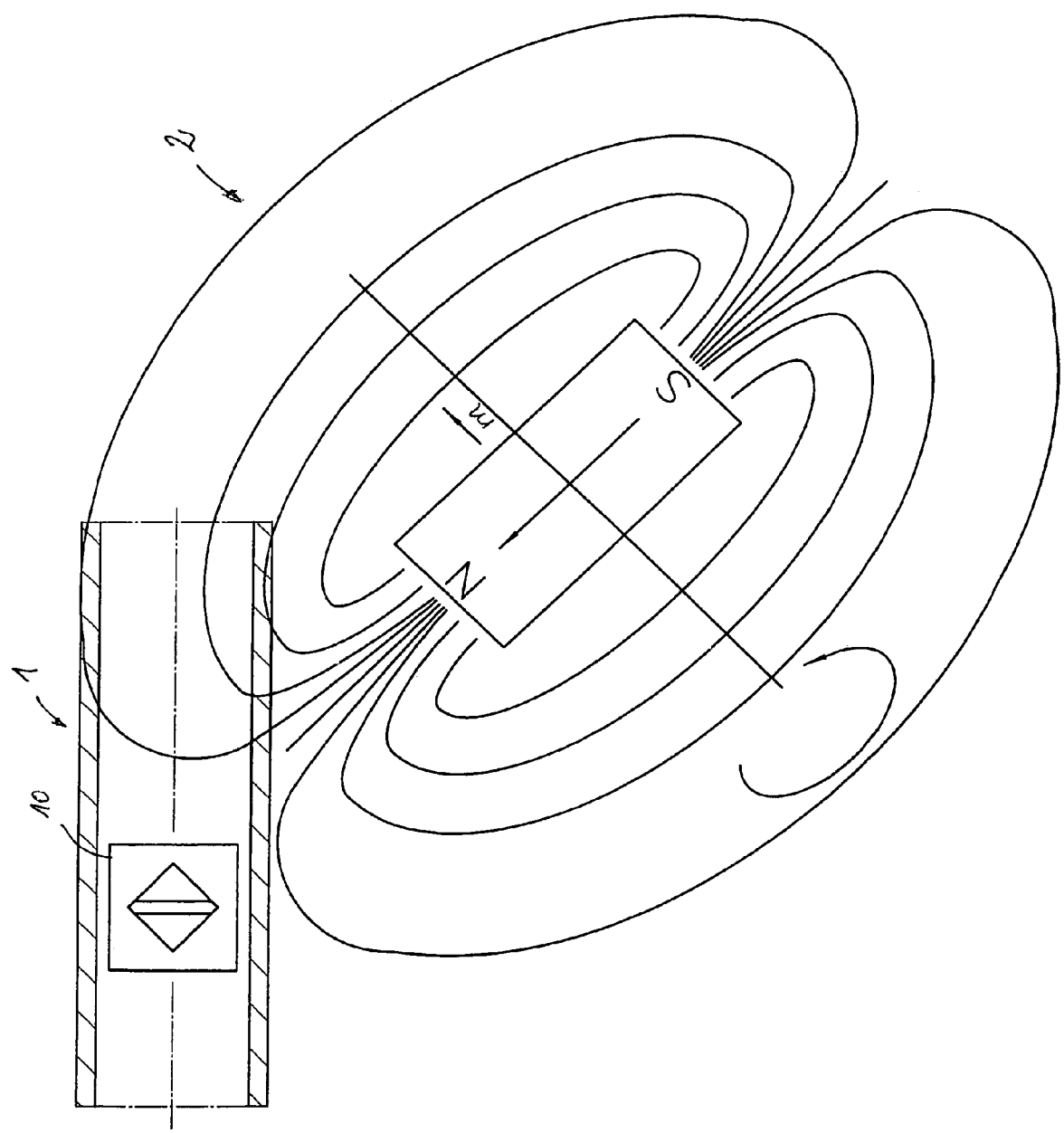
FIG. 13 is a schematic illustration of a variation of another apparatus embodying the subject matter of the present invention.

Referring now to FIG. 13, there is shown a schematic illustration of a variation of another apparatus, involving the arrangement of a magnetic field sensor 10 which is mounted in the longitudinal axis L of the instrument 1, and a magnet 2 which is outside of the instrument separate from the longitudinal axis L.

Figure 14:
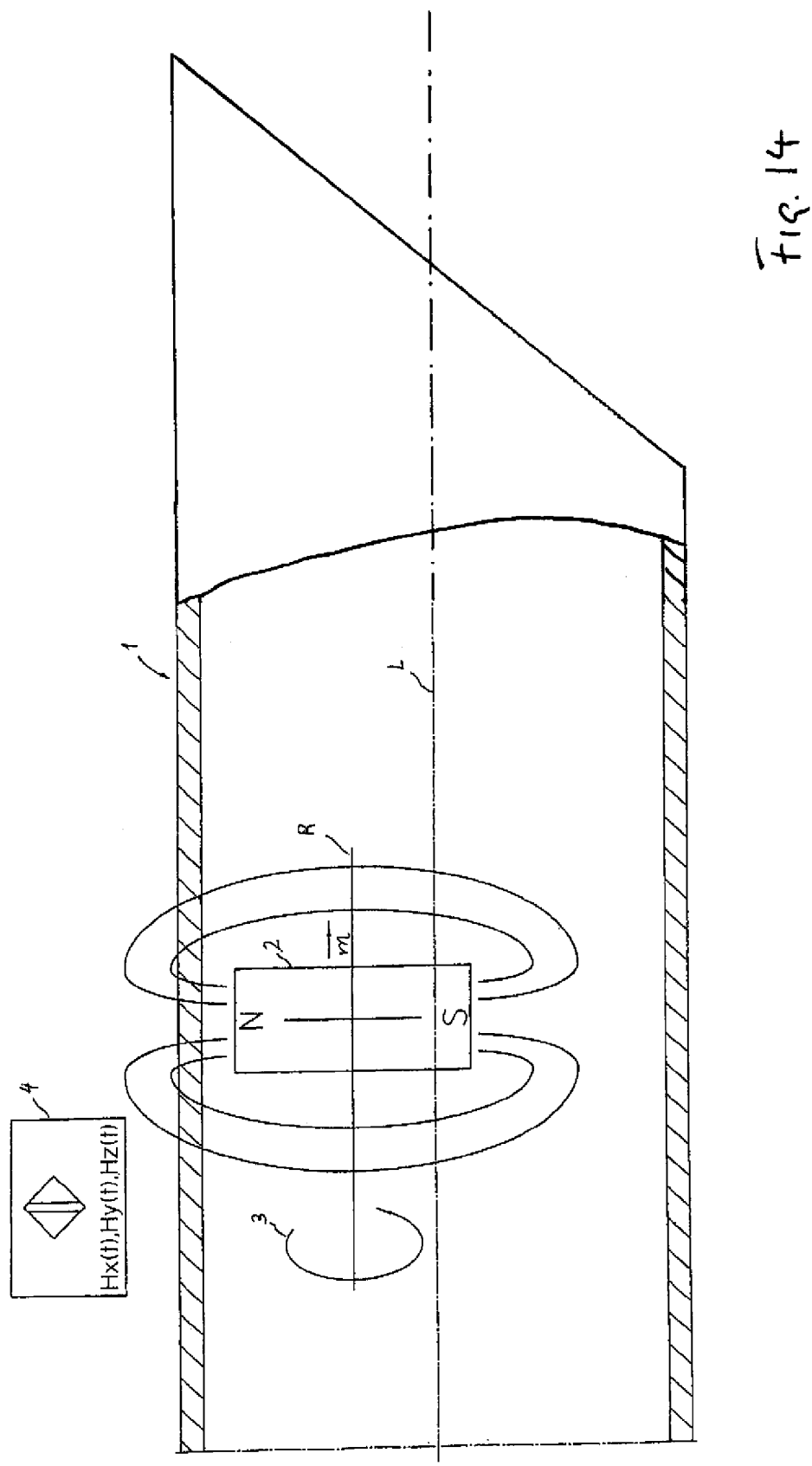
FIG. 14 is a sectional view of the apparatus of FIG. 1, illustrating an instrument provided with a drill.
Figure 15:
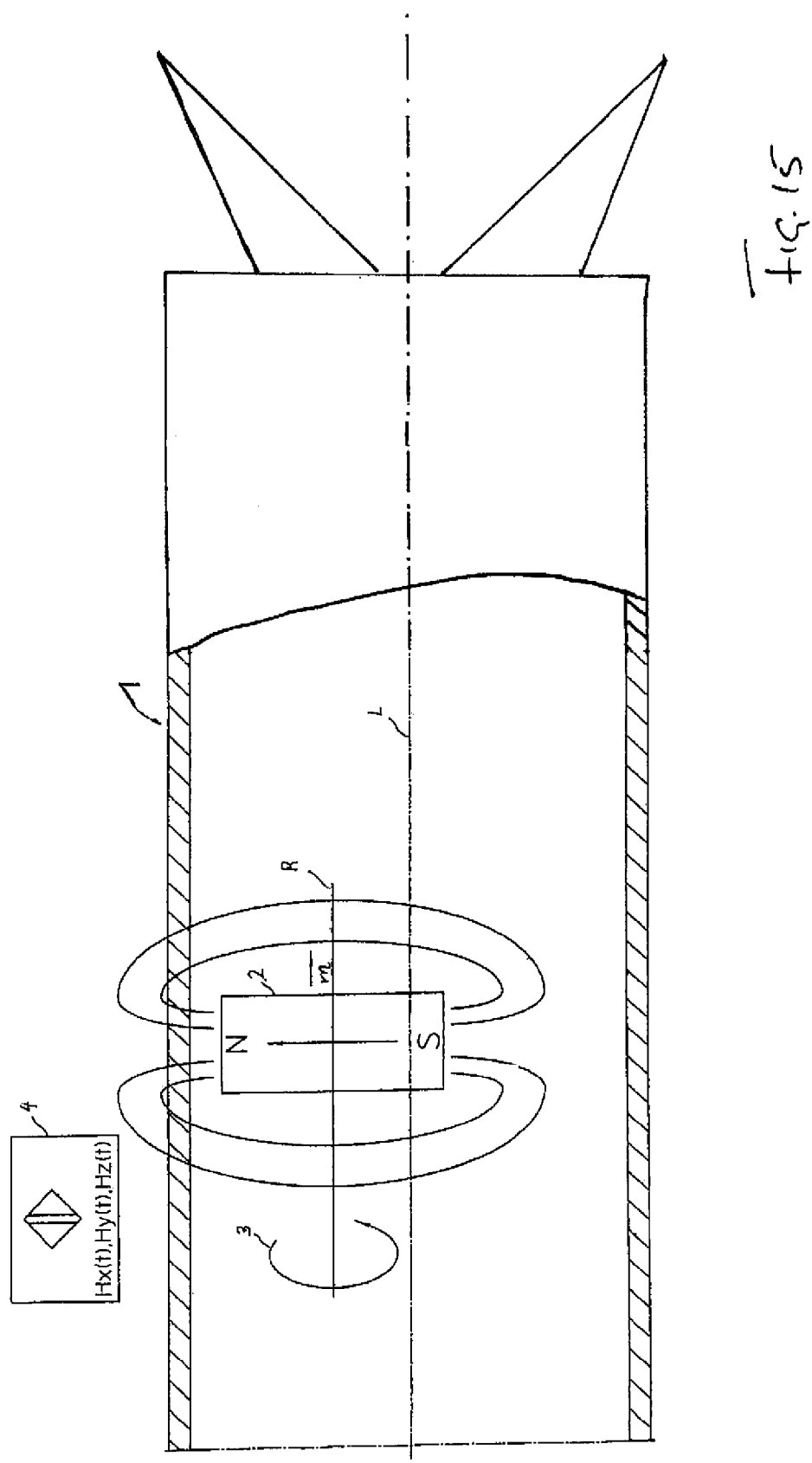
FIG. 15 is a sectional view of the apparatus of FIG. 1, illustrating an instrument provided with a set of forceps.

FIGS. 14-16 show variations of the instrument 1, whose tip is provided with at least one drill, a culling or impact apparatus, a needle, a canular or a set of forceps.

What is claimed is:

1. An apparatus for locating an instrument, comprising:
   an instrument having a body;
   at least one magnet disposed inside the body of the instrument, the at least one magnet being rotatable independently of a rotation of the body of the instrument and adapted to produce a moving magnetic field extending outside the body of the instrument to generate a magnetic moment which is perpendicular to an axis of the instrument;
   a drive for rotating the at least one magnet independent of the body of the instrument;
   variation means for varying the magnetic field generated outside the body of the instrument by the at least one magnet, thereby creating a variable magnetic field component which relates to a roll angle of the instrument; and
   a receiver outside the body of the instrument configured for measuring the variable magnetic field component to determine the roll angle of the instrument.

2. The apparatus as claimed in claim 1, wherein the receiver is configured to detect three time-dependent magnetic field components.

3. The apparatus as claimed in claim 1, further comprising an evaluation unit for determining from the variable magnetic field component at least one parameter selected from the group consisting of position, direction of the instrument axis, and roll angle of the instrument.

4. The apparatus as claimed in claim 1, wherein the drive is an electrical drive.

5. The apparatus as claimed in claim 1, wherein the drive is a hydraulic drive using liquid to drive the magnet.

6. The apparatus as claimed in claim 1, further comprising means for providing a reproducible deflection of the magnet from its rotation axis.

7. The apparatus as claimed in claim 1, further comprising a coupling which temporarily interrupts the rotation of the magnet.

8. The apparatus as claimed in claim 1, wherein the magnet is composed of magnet elements that move with respect to one another and whose elements are shifted by a driver at a specific roll angle.

9. The apparatus as claimed in claim 1, wherein the instrument has a member selected from the group consisting of drill, culling or impact apparatus, at least one needle, and at least one set of forceps.

10. The apparatus as claimed in claim 1, wherein the instrument has at least one opening for ejection of a liquid.

11. The apparatus as claimed in claim 1, wherein the instrument has an apparatus for production/emission of light beams, laser beams, radioactive beams, sound waves or ultrasound waves.

12. The apparatus as claimed in claim 1, wherein the instrument has an apparatus for recording optical images or ultrasound images.

13. The apparatus as claimed in claim 1, wherein the instrument has an apparatus for emission of electrical pulses or for recording electrical data.

14. The apparatus as claimed in claim 1, further comprising two or more transmitters and/or additional receivers for processing signals commensurate with a position of the instrument at different points.

15. The apparatus as claimed in claim 14, wherein each transmitter is constructed as a permanent magnet and/or electromagnet and configured for a transmitter identification by different frequencies, amplitudes and/or by the production of different analog or digital values.

16. The apparatus as claimed in claim 1, further comprising a frequency modulation for varying the magnetic field generated by the magnet.

17. The apparatus as claimed in claim 1, further comprising a gradual shielding of the magnet.

18. A method of determining a location of an instrument, comprising the steps of:

rotating at least one magnet disposed inside a body of the instrument independent of a rotation of the instrument to produce a magnetic field to generate a magnetic moment outside the body of the instrument perpendicular to an axis of the instrument;

detecting three time-dependent magnetic field components of the magnetic field;

modulating a frequency of the rotation for variation of the magnetic field generated by the magnet to minimize the influence of a disturbing external magnetic field or to distinguish the magnetic field from another magnetic field; and determining a location of the instrument based on the detected magnetic field components.

19. A method of determining a location of an instrument, comprising the steps of:

producing a magnetic field by a rotating magnet inside a body of the instrument independent of a rotation of the body of the instrument to generate a magnetic moment perpendicular to an axis of the instrument, with the magnet configured as a transmitter;

detecting with a receiver three time-dependent magnetic field components produced by the rotating magnet outside the body of the instrument; and modulating a frequency of the rotation for variation of the magnetic field generated by the magnet to minimize the influence of a disturbing external magnetic field or to distinguish the magnetic field from another magnetic field; and determining a location of the instrument based on the detected magnetic field components.

* * * * *